(12) United States Patent
Kwong

(10) Patent No.: US 10,092,595 B2
(45) Date of Patent: Oct. 9, 2018

(54) COMPOSITIONS AND METHODS FOR TREATING INFLAMMATORY ARTHRITIS

(75) Inventor: Yok-Lam Kwong, Midlevels (HK)

(73) Assignee: The University of Hong Kong, Hong Kong (HK)

( * ) Notice: Subject to any disclaimer, the term of this patent is extended or adjusted under 35 U.S.C. 154(b) by 192 days.

(21) Appl. No.: 12/781,970

(22) Filed: May 18, 2010

(65) Prior Publication Data

US 2010/0291234 A1 Nov. 18, 2010

Related U.S. Application Data

(60) Provisional application No. 61/179,147, filed on May 18, 2009.

(51) Int. Cl.
| | | |
|---|---|---|
| *A61K 31/285* | (2006.01) | |
| *A61P 19/02* | (2006.01) | |
| *A61P 29/00* | (2006.01) | |
| *C12N 5/071* | (2010.01) | |
| *A61K 33/24* | (2006.01) | |
| *A61K 45/06* | (2006.01) | |
| *C12N 5/077* | (2010.01) | |

(52) U.S. Cl.
CPC .............. *A61K 33/24* (2013.01); *A61K 45/06* (2013.01); *C12N 5/0655* (2013.01); *C12N 2501/48* (2013.01); *C12N 2501/999* (2013.01)

(58) Field of Classification Search
None
See application file for complete search history.

(56) References Cited

U.S. PATENT DOCUMENTS

2008/0089951 A1* 4/2008 Kwong .................... 424/623
2008/0193560 A1* 8/2008 Hwang et al. ............. 424/623

OTHER PUBLICATIONS

Smolen et al. "Effect of interleukin-6 receptor inhibition with tocilizumab in patients with rheumatoid arhritis (OPION study): a double-blind, placebo-controlled, randomised trial", The Lancet, 371, 2008, pp. 987-997.*
Pope, "Apoptosis as atherapeutic tool in rheumatoid arhritis", Nature Reviews immunology, 2, 2002, pp. 1-9.*
Feng et al. "As2O3 induces synoviocyte apoptosis of rheumatoid arthritis in vitro" Journal of Bethune Medical University, 26(3), 2000, pp. 260-262.*
Au et al., "Oral arsenic trioxide in the treatment of relapsed acute promyelocytic leukemia", Blood, 102(1), 2003, pp. 407-408.*
Amano, et al., "Synoviolin/Hrd1, an E3 ubiquitin ligase, as a novel pathogenic factor for arthropathy", Genes Dev., 17:2436-49 (2003).
Au, et al., "Determinants of cerebrospinal fluid arsenic concentration in patients with acute promyelocytic leukemia on oral arsenic trioxide therapy", Blood, 112:3587-90 (2008).
Cheung, et al., "Effects of arsenic trioxide on the cellular proliferation, apoptosis and differentiation of human neuroblastoma cells", Cancer Lett., 246:122-8 (2007).
Choy, et al., "Cytokine pathways and joint inflammation in rheumatoid arthritis", N. Engl. J. Med., 344:907-16 (2001).
Davison, et al., "JNK activation is a mediator of arsenic trioxide-induced apoptosis in acute promyelocytic leukemia cells", Blood, 103:3496-502 (2004).
Harigai, et al., "Pneumocystis pneumonia associated with infliximab in Japan", N. Engl. J. Med., 357:1874-6 (2007).
Heinrich, et al., "Principles of interleukin (IL)-6-type cytokine signalling and its regulation", Biochem. J., 374:1-20 (2003).
Keane, et al., "Tuberculosis associated with infliximab, a tumor necrosis factor alpha-neutralizing agent", N. Engl. J. Med., 345:1098-104 (2001).
Kitano, et al., "Sphingosine 1-phosphate/sphingosine 1-phosphate receptor 1 signaling in rheumatoid synovium: regulation of synovial proliferation and inflammatory gene expression", Arthritis Rheum., 54:742-53 (2006).
Lee, et al., "Cadherin-11 in synovial lining formation and pathology in arthritis", Science, 315:1006-10 (2007).
Lipsky, "Why does rheumatoid arthritis involve the joints", N. Engl. J. Med., 356:2419-20 (2007).
Lipsky, et al., "Infliximab and methotrexate in the treatment of rheumatoid arthritis. Anti-Tumor Necrosis Factor Trial in Rheumatoid Arthritis with Concomitant Therapy Study Group", N. Engl. J. Med., 343:1594-602 (2000).
Liu and Lin, "Wiring the cell signaling circuitry by the NF-kappa B and JNK1 crosstalk and its applications in human diseases", Oncogene, 26:3267-78 (2007).
Marmor and Yarden, "Role of protein ubiquitylation in regulating endocytosis of receptor tyrosine kinases", Oncogene, 23:2057-70 (2004).
Miyazawa, et al., "Establishment and characterization of a novel human rheumatoid fibroblast-like synoviocyte line, MH7A, immortalized with SV40 T antigen", J. Biochem., 124:1153-62 (1998).
Naka and Kishimoto, "Joint disease caused by defective gp130-mediated STAT signaling", Arthritis Res., 4:154-6 (2002).
Nishimoto, et al., "Lack of association between PADI4 and functional severity in Japanese rheumatoid arthritis patients", Ann. Rheum Dis., 67(3):431-32 (2008).
Simmonds and Foxwell, "Signalling, inflammation and arthritis: NF-kappaB and its relevance to arthritis and inflammation", Rheumatology, 47:584-90 (2008).
Siu, et al., "Effects of oral arsenic trioxide therapy on QT intervals in patients with acute promyelocytic leukemia: implications for long-term cardiac safety", Blood, 108:103-6 (2006).
Smolen, et al., "Effect of interleukin-6 receptor inhibition with tocilizumab in patients with rheumatoid arthritis (OPTION study): a double-blind, placebo-controlled, randomised trial", Lancet, 371:987-97 (2008).
Tarner, et al., "Emerging targets of biologic therapies for rheumatoid arthritis", Nat. Clin. Pract. Rheumatol., 3:336-45 (2007).
Wu, "The functional interactions between the p53 and MAPK signaling pathways", Cancer Biol. Ther., 3:156-61 (2004).
Young and McGwire, et al., "Infliximab and reactivation of cerebral toxoplasmosis", N. Engl. J. Med., 353:1530-1 (2005).

* cited by examiner

*Primary Examiner* — Melissa L Fisher
(74) *Attorney, Agent, or Firm* — Pabst Patent Group LLP

(57) ABSTRACT

Methods for treating or preventing one or more symptoms of rheumatoid arthritis or other types of inflammatory arthritis involves administering a formulation containing an effective amount of arsenic trioxide to an affected patient. The arsenic trioxide formulation can be administered orally, for example, as a solution, suspension, syrup, emulsion, tablet, or capsule.

22 Claims, 9 Drawing Sheets
Specification includes a Sequence Listing.

COMPOSITIONS AND METHODS FOR TREATING INFLAMMATORY ARTHRITIS

CROSS REFERENCE TO RELATED APPLICATIONS

This application claims benefit of U.S. Provisional Application No. 61/179,147, filed May 18, 2009, which is incorporated herein by reference in its entirety.

FIELD OF THE INVENTION

The present disclosure generally relates to the field of methods for treating rheumatoid arthritis and other inflammatory arthritis using arsenic trioxide.

BACKGROUND OF THE INVENTION

Rheumatoid arthritis (RA) is an autoimmune arthropathy associated with systemic inflammatory manifestations. In RA, the synovium, the inner lining of synovial joints, is abnormal. There is infiltration of acute inflammatory cells in the synovium, which undergoes hypertrophy, resulting in effusion of the joint. Hyperplastic synovium may also lead to erosion of the adjacent cartilage and bone, causing joint destruction. The end result is joint inflammation, effusion, joint and adjacent ligament destruction, joint deformity and, finally, loss of function. RA is the most common inflammatory joint disease, affecting virtually all populations in the world. It is a serious worldwide health problem.

Traditional treatment of RA centers on the use of antiinflammatory drugs to suppress joint inflammation and production of cytokines. Immunomodulatory drugs may also be effective, including immunosuppressive drugs such as corticosteroids, methotrexate and cyclosporine (Tamer, et al., *Nat. Clin. Pract. Rheumatol.*, 3:336-45 (2007)). Other disease modifying medications including penicillamine and gold may also be used.

The pathogenesis of RA is complex and has not been fully defined. However, a number of cytokines, including interleukin (IL)-6, IL-15, IL-17, and tumor necrosis factor, have been implicated in causing joint and systemic inflammation (Tamer, et al., *Nat. Clin. Pract. Rheumatol.*, 3:336-45 (2007)). The cytokine signaling pathways incriminated in RA pathogenesis include the tumor necrosis factor alpha (TNF-α) pathway, the mitogen activated protein kinase (MAPK) pathway, the Janus kinases (JAK) pathway, and the signal transducer and activator of transcription (STAT) pathways. An important molecule downstream of TNF-α pathway is the transcription factor nuclear factor kappa B (NFκB). These pathways play important parts in the synovial proliferation, and the consequent joint damage characteristic of RA (Tamer, et al., *Nat. Clin. Pract. Rheumatol.*, 3:336-45 (2007)).

Recently, it has also been shown that the synovium plays an active role in joint inflammation. Fibroblast-like synoviocytes are the most important cellular component of the synovium. Synoviocytes are necessary for the initiation and propagation of the inflammation observed in RA, mediating both cartilage damage and acute and chronic inflammation (Lipsky, *N. Engl. J. Med.*, 356:2419-20 (2007)). The importance of the synoviocytes is further shown by the finding that mouse models deficient in a functional synovium are resistant to experimental arthritis (Amano, et al., *Genes Dev.*, 17:2436-49 (2003); Lee, et al., *Science*, 315:1006-10 (2007)).

Targeting of two of the key pathways involved putatively in RA pathogenesis has shown that this may be a potential therapeutic strategy (Choy, et al., *N. Engl. J. Med.*, 344:907-16 (2001)). Treatment with infliximab, a chimeric monoclonal antibody against TNF-α, results in significant improvement in joint inflammation and halts the progression of joint damage (Lisky, et al., *N. Engl. J. Med.*, 343:1594-602 (2000)). Treatment with tocilizumab, an antibody against the IL-6 receptor (IL-6R), leads to significant control of symptoms in RA patients (Smolen, et al., *Lancet*, 371:987-97 (2008)).

The use of infliximab, however, has been associated with tuberculosis (Keane, et al., *N. Engl. J. Med.*, 345:1098-104 (2001)), and other opportunistic infections including pneumocystis pneumonia (Harigai, et al., *N. Engl. J. Med.*, 357:1874-6 (2007))) and cerebral toxoplasmosis (Young, et al., *N. Engl. J. Med.*, 353:1530-1 (2005)). Serious infections have also happened to patients on tocilizumab treatment (Nishimoto, et al., *Ann. Rheum Dis.*, (2008)). These medications are also expensive. Moreover, because they are given intravenously, they are expensive and cumbersome for the patient.

Therefore, it is an object of the invention to provide formulations and methods for suppressing the growth and activity of synoviocytes in rheumatoid arthritis. Because synoviocytes may also play important pathogenetic roles in other inflammatory arthritis, it is another object of the invention to provide formulations and methods for suppressing the growth and activity of synoviocytes in other inflammatory arthritis.

It is yet another object of the invention to provide formulations and methods for treating inflammatory arthritis.

SUMMARY OF THE INVENTION

It has been discovered that $As_2O_3$ reduces the growth of synoviocytes associated with rheumatoid arthritis. $As_2O_3$ leads to a decrease in levels of gp130, a component of the IL-6 receptor complex, by targeting gp130 to destruction in the lysosome, thereby disrupting an autocrine IL-6 loop in synovial cells.

Methods for inhibiting or reducing the growth of synoviocytes using $As_2O_3$ are provided. Also provided are methods for treating or preventing one or more symptoms of rheumatoid arthritis and other inflammatory arthritis using formulations containing $As_2O_3$.

DETAILED DESCRIPTION OF THE INVENTION

I. Arsenic Trioxide Formulations

A. Arsenic Trioxide

Figure 1A:
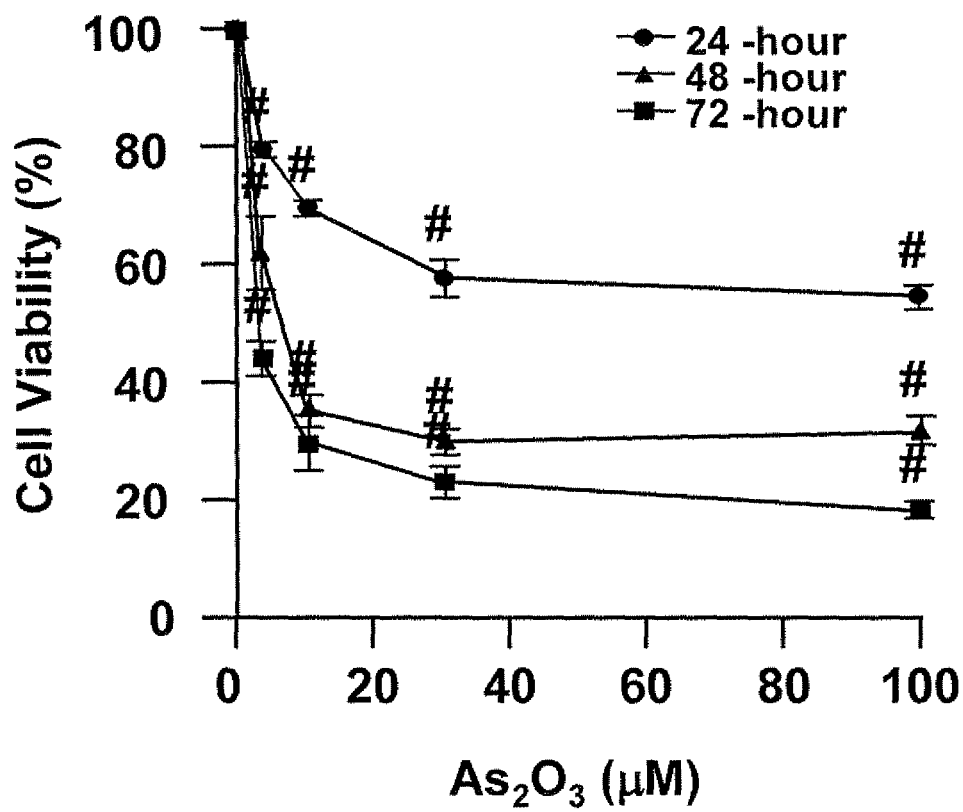
FIG. 1A is a line graph showing the effects of increasing concentrations of arsenic trioxide ($As_2O_3$) on growth of MH7A cells when treated for 24 (-•-), 48 (-▲-) or 72 (-■-) hours, as assessed by MIT assays. Data are expressed as cell viability (%) as a function of $As_2O_3$ concentration (μM). Error bars represent the standard error of the mean (SEM) (n=3) (#=P<0.001)

Arsenic trioxide is very useful in the treatment of refractory promyelocytic (M3) subtype of acute myeloid leukemia. An oral arsenic trioxide ($As_2O_3$) is highly efficacious for relapsed acute promyelocytic leukemia. (Au, et al., *Blood*, 112:3587-90 (2008)) Oral $As_2O_3$ causes a smaller prolongation of QT intervals, and therefore is a much safer drug for treating leukemia. Recently, it was also demonstrated that oral $As_2O_3$ produces minimal QT prolongation in the heart, meaning that it is safe for prolonged use (Siu, et al., *Blood*, 108:103-6 (2006)).

B. Formulations

The following delivery systems are representative of formulations for administering the $As_2O_3$.

1. Parenteral Formulations

Injectable drug delivery systems include pharmaceutically acceptable solutions, suspensions, gels, microspheres and implants. Typically these will be in the form of distilled water, phosphate buffered saline, or other vehicle for injection intravenously or subcutaneously.

2. Enteral Formulations

Oral delivery systems include solutions, suspensions, and solid dosage forms such as tablets (e.g, compressed tablets, sugar-coated tablets, film-coated tablets, and enteric coated tablets), capsules (e.g., hard or soft gelatin or non-gelatin capsules), blisters, and cachets. These can contain excipients such as binders (e.g., hydroxypropylmethylcellulose, polyvinyl pyrilodone, other cellulosic materials and starch), diluents (e.g., lactose and other sugars, starch, dicalcium phosphate and cellulosic materials), disintegrating agents (e.g., starch polymers and cellulosic materials) and lubricating agents (e.g., stearates and talc). The solid dosage forms can be coated using coatings and techniques well known in the art.

Oral liquid dosage forms include solutions, syrups, suspensions, emulsions, elixirs (e.g., hydroalcoholic solutions), and powders for reconstitutable delivery systems. The formulations can contain one or more carriers or excipients, such as suspending agents (e.g., gums, zanthans, cellulosics and sugars), humectants (e.g., sorbitol), solubilizers (e.g., ethanol, water, PEG, glycerin, and propylene glycol), surfactants (e.g., sodium lauryl sulfate, Spans, TWEENs, and cetyl pyridine), emulsifiers, preservatives and antioxidants (e.g., parabens, vitamins E and C, and ascorbic acid), anti-caking agents, coating agents, chelating agents (e.g., EDTA), flavorants, colorants, and combinations thereof.

3. Topical Formulations

Transmucosal delivery systems include patches, tablets, suppositories, pessaries, gels and creams, and can contain excipients such as solubilizers and enhancers (e.g., propylene glycol, bile salts and amino acids), and other vehicles (e.g., polyethylene glycol, fatty acid esters and derivatives, and hydrophilic polymers such as hydroxypropylmethylcellulose and hyaluronic acid).

Dermal delivery systems include, for example, aqueous and nonaqueous gels, creams, multiple emulsions, microemulsions, liposomes, ointments, aqueous and nonaqueous solutions, lotions, aerosols, hydrocarbon bases and powders, and can contain excipients such as solubilizers, permeation enhancers (e.g., fatty acids, fatty acid esters, fatty alcohols and amino acids), and hydrophilic polymers (e.g., polycarbophil and polyvinylpyrolidone). In one embodiment, the pharmaceutically acceptable carrier is a liposome or a transdermal enhancer.

II. Methods of Treatment

A. Treatment of Rheumatoid Arthritis $As_2O_3$ formulations are administered to an individual having RA in an effective amount to inhibit or reduce the proliferation of synoviocytes, to inhibit or reduce cell surface expression of the IL-6 receptor in synovial cells, or in an effective amount to treat or reduce the risk of developing one or more symptoms of rheumatoid arthritis. The disclosed $As_2O_3$ formulations can be administered therapeutically or prophylactically.

Therapeutically effective amounts of the disclosed $As_2O_3$ formulations refers to amounts effective to delay progression, expedite remission, induce remission, augment remission, speed recovery, increase efficacy of or decrease resistance to alternative therapeutics, or a combination thereof. Therapeutically effective amounts can be effective in reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, or a combination thereof.

Prophylactically effective amounts of the $As_2O_3$ formulations refers to amounts effective to delay the onset of symptoms, prevent relapse to a disease, decrease the number or frequency of relapse episodes, increasing latency between symptomatic episodes, or a combination thereof.

The examples below use MH7A as a model of RA synovium, since MH7A retains most of the biological properties of fibroblast-like synoviocytes, including surface immunophenotype and response to cytokines (Miyazawa, et al., *J. Biochem.*, 124:1153-62 (1998)). Cellular signaling and gene expression patterns of MH7A cells are also similar to primary RA synoviocytes (Kitano, et al., *Arthritis Rheum.*, 54:742-53 (2006)). Using this model, it was discovered that $As_2O_3$ is effective to inhibit the proliferation of fibroblast synoviocytes implicated in the development of rheumatoid arthritis.

The examples below also demonstrate that an autocrine IL-6 loop functions in MH7A cells, as shown by expression of both IL-6 and IL-6 receptor, and that IL-6 neutralization significantly inhibits MH7A cellular proliferation. IL-6 signals by binding to the IL-6 receptor complex, which comprises an 80-kDa IL-6 binding protein (IL-6 receptor α) and a 130 kDa signal transducer gp130 (Naka and Kishimoto, *Arthritis Res.*, 4:154-6 (2002)).

The examples also demonstrate that an autocrine IL-6 loop functions in MH7A cells, as shown by expression of both IL-6 and IL-6 receptor, and that IL-6 neutralization significantly inhibits MH7A cellular proliferation. IL-6 signals by binding to the IL-6 receptor complex, which comprises an 80-kDa IL-6 binding protein (IL-6 receptor α) and a 130 kDa signal transducer gp130 (Naka and Kishimoto, Arthritis Res., 4:154-6 (2002)). The examples demonstrate that $As_2O_3$ treatment leads to a time and dose dependent decrease in gp130 cell surface expression post-transcriptionally. Through the use of specific inhibitors, the examples show that $As_2O_3$-mediated decreases of gp130 are regulated by the lysosome and not the proteasome or caspase systems. The examples also show that gp130 degradation is initiated by mono-ubiquitination, a process that provides a biologic signal leading to sorting of the receptors for degradation in the lysosomes (Marmor and Yarden, Oncogene, 23:2057-70 (2004)).

B. Methods of Administration

The $As_2O_3$ formulations can be administered before, during or after the onset of symptoms associated with rheumatoid arthritis. Any acceptable method known to one of ordinary skill in the art can be used to administer the disclosed $As_2O_3$ formulations to a subject.

The administration can be localized (i.e., to a particular region, physiological system, tissue, organ, or cell type) or systemic. $As_2O_3$ formulations can be administered by different routes, such as oral, parenteral and topical. The $As_2O_3$ formulations can also be administered directly to a joint, especially a synovial joint. The particular route of administration selected will depend upon factors such as the particular formulation, the severity of the state of the subject being treated, and the dosage required to induce an effective immune response.

In a preferred embodiment, the $As_2O_3$ formulations are administered orally. Effective oral dosages of $As_2O_3$ range from about 0.5 mg to about 1 to 10 mg, typically about 5 to 10 mg depending on the age if the subject and their kidney function. $As_2O_3$ is excreted via the kidneys, and therefore $As_2O_3$ dosage has to be adjusted according to the renal function, lowering the dosage where renal function of the patient is impaired.

An effective level of the $As_2O_3$ formulation can be ideally obtained after one single administration. In certain circumstances, it can be beneficial to administer two or more doses of $As_2O_3$ formulations.

C. Combination Therapy

The $As_2O_3$ formulations can be administered alone or in combination with one or more additional therapeutic or prophylactic agents, or can be coupled with surgical, radiologic, or other approaches in order to affect treatment. For example, the $As_2O_3$ formulations can be administered in combination with one or more anti-inflammatory agents.

Anti-inflammatory agents can be non-steroidal, steroidal, or a combination thereof. Representative examples of non-steroidal anti-inflammatory agents include, without limitation, oxicams, such as piroxicam, isoxicam, tenoxicam, sudoxicam; salicylates, such as aspirin, disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone. Mixtures of these non-steroidal anti-inflammatory agents can also be employed.

Representative examples of steroidal anti-inflammatory drugs include, without limitation, corticosteroids such as hydrocortisone, hydroxyl-triamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluadrenolone, fludrocortisone, difluorosone diacetate, fluadrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

EXAMPLES

Example 1. Inhibition of MH7A Cell Proliferation by $As_2O_3$

Materials and Methods:

Fibroblast-Like Synoviocyte MH7A Cell Line

MH7A was purchased from the Riken BioResource Center (Tsukuba, Japan). Cells were maintained in RPMI1640 (Invitrogen, Carlsbad, Calif., USA) supplemented with 10% heat inactivated fetal bovine serum (FBS; Invitrogen) in 5% $CO_2$ at 37° C.

Reagents and Antibodies

Reagents included $As_2O_3$ and dimethylsulphoxide (DMSO) (Sigma, St. Louis, Mo., USA), ammonium chloride ($NH_4Cl$) (Amresco, Solon, Ohio, USA), the proteasome inhibitor MG115, pan-caspase inhibitor Z-VAD-FMK, JNK inhibitor SP600125 and its negative control (Merck, Darmtadt, Germany), and recombinant human IL-6 (Peprotech, Rocky Hill, N.J., USA). Primary antibodies included rabbit anti-IL-6 receptor α (IL-6Rα) and gp130 (C-20) antibodies (Santa-Cruz Biotechnology, Santa Cruz, Calif., USA), rabbit-IL-6 antibody (Merck), rabbit anti-phosphorylated JNK ($Thr^{183}/Tyr^{185}$), anti-caspase 3, anti-β-actin and anti-NFκB antibodies (Cell Signaling Technology, Beverly, Mass., USA), and mouse anti-ubiquitin antibodies FK1 and FK2 (Biomol, Plymouth Meeting, Pa., USA). Secondary antibodies included horseradish peroxide conjugated goat anti-rabbit IgG and rabbit anti-mouse IgG (Invitrogen).

MTT Assay

Cellular proliferation was assessed by an MTT assay (GE Healthcare, Piscataway, N.J., USA) (Cheung et al., Cancer Lett., 246:122-8 (2007)). Cells ($2 \times 10^4$ cells/well in 96-well plates) were incubated overnight before treatment with controls or reagents for 2-6 days. The treated cells were then incubated with the MTT labeling solution (10 μL/well). After 4 hours of incubation, cells were lyzed, and formazan crystals solubilized overnight at 37° C. Formazean signal was detected at 570 nm (μ-Quant™ microplate spectrometer, Bio-Tek Instruments Inc., VT, USA). Data obtained were analyzed by the KC junior software (BLD Science, Garner, N.C., USA).

Western Blot Analysis

Western blot analysis was performed (Pang et al., Gastroenterology, 132:1088-103 (2007)). Cell lysis and protein collection was conducted according to standard protocols. Protein samples (typically 30 μg) were separated by sodium dodecyl sulfate-polyacrylamide gel electrophoresis (SDS-PAGE) in 12% resolving gel and electro-transferred to nitrocellulose membranes (400 mA for 2 hours). After blocking with tris-buffered saline-TWEEN (TBS-T) containing 5% non-fat milk at room temperature for 30 minutes, membranes were incubated with the primary antibody and TBS-T with 5% bovine serum albumin at 4° C. overnight. The membranes were then washed thrice with TBS-T, and incubated for 1 hour at room temperature with 1:2000 horseradish peroxidase-conjugated secondary antibodies (Amersham-Pharmacia Biotechnology, Piscataway, N.J., USA). Immunoreactive bands were detected with chemiluminescence using the SuperSignal West Pico Chemiluminescent Substrate (Pierce Chemical Co., Rockford, Ill., USA), and visualized on X-ray films. Densitometric quantification of band signals was performed using ImageJ 1.36b software (National Institutes of Health, USA). All experiments were performed in triplicates.

Annexin V Apoptosis Assay

For apoptosis assay, $1 \times 10^6$ cells were incubated in 10-cm plates overnight, before treatment with controls or reagents for 24 hours. Cells were then trypsinized, washed twice with ice-cold phosphate buffered saline (PBS), re-suspended in 500 μL of binding buffer, and incubated on ice for 10 minutes with FITC-conjugated annexin-V and propidium iodide (PI) (Immunotech; Fullerton, Calif., USA). Apoptotic cells (annexin-V-positive, PI-negative) were enumerated by flow cytometry in triplicates (Epics, Beckman Coulter, Fullerton, Calif., USA) after appropriate color compensation. Data analysis was performed by the WinMDI 2.8 software (The Scripps Research Institute, La Jolla, Calif., USA).

Results:

$As_2O_3$ induced a dose and time dependent inhibition of growth of MH7A cells (FIG. 1A), with a 50% inhibitory concentration at about 5 μM. Flow cytometric analysis confirmed that inhibition of cellular growth was mediated by induction of apoptosis. MH7A cells were incubated with $As_2O_3$ (5 μM) for 0-24 hours, and stained with propodium iodide (PT) and annexin-V to distinguish between apoptotic cells and dead cells. In a representative assays, 13% of control cells were annexin-V positive, propidium iodide negative (apoptotic) and 2.36% were annexin-V positive, popidium iodide positive (dead), while 38.2% of treated cells were annexin-V positive, propidium iodide negative (apoptotic) and 5.76% were annexin-V positive, popidium iodide positive (dead). Results of the FACS analysis shows an increase in apoptotic cells after $As_2O_3$ treatment.

Figure 1B:
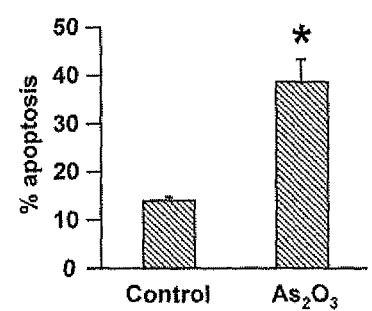
FIG. 1B is a bar graph showing the percent of apoptosis in the absence or presence of 5 μM $As_2O_3$, as determined by FACS analysis of MH7A cells following propidium iodide (PI) and annexin-V staining. Apoptotic cells were
Figure 1C:
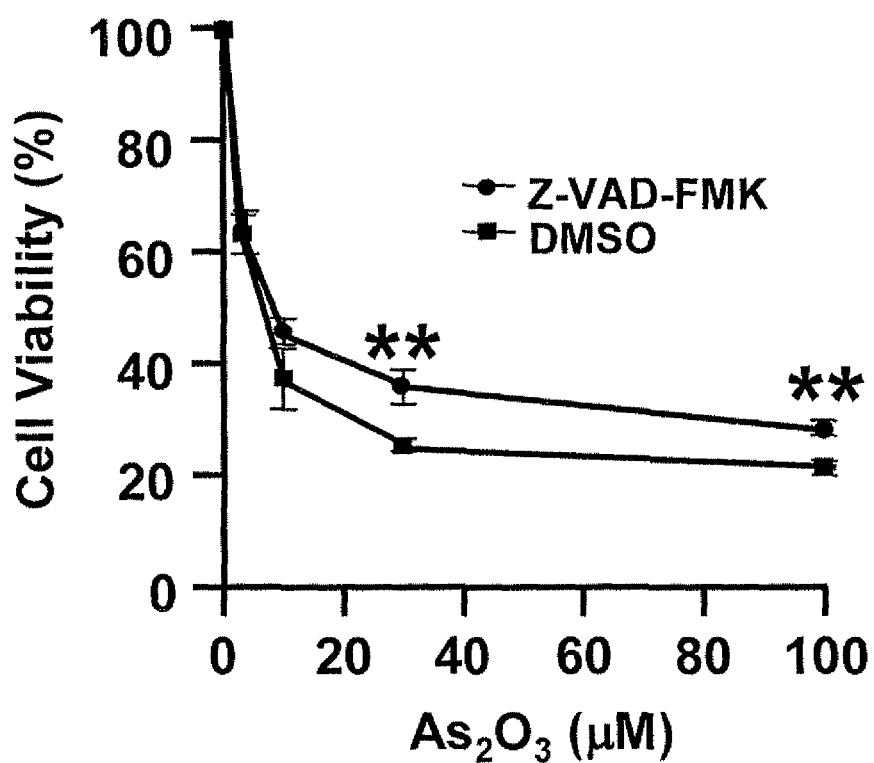
FIG. 1C is a line graph showing viability of MH7A cells in the presence (-•-) or absence (-■-) of the pan-caspase inhibitor Z-VAD-FMK (25 μM) and in the presence of increasing concentrations of $As_2O_3$ over 72 hours, as assessed by MTT assays. Data are expressed as cell viability (%) as a function of $As_2O_3$ concentration (μM). Error bars represent the standard error of the mean (SEM) (n=3) (**=P<0.01).

Western blot analysis showed that $As_2O_3$ induced a dose and time dependent activation of caspase 3. Inhibition of caspase 3 by the caspase inhibitor Z-VAD-FMK (25 μM) significantly reduced but did not totally ameliorate the cytotoxic effect of $As_2O_3$ (FIG. 1C). The results implied that both caspase-dependent and caspase-independent pathways were involved in As$_2$O$_3$-induced cytotoxicity in MH7A.

Example 2. Inhibition of MH7A Cell Proliferation by an Il-6 Neutralizing Antibody Materials and Methods:
Reverse Transcription Polymerase Chain Reaction (RT-PCR)

Total RNA was prepared using TRIzol (Invitrogen). Reverse transcription PCR (RT-PCR) was performed (Cheung, et al., *Cancer Lett.*, 246:122-8 (2007)). RNA was reverse transcribed with the Superscript™ III First-Strand Synthesis System (Invitrogen) according to the manufacturer's instructions. Reaction mixes contained 1.2 µL of cDNA, 18 µL of Platinum® PCR Supermix (Invitrogen) and 200 nM of each pair of primers. Annealing temperatures and number of amplification cycles performed for each set of primers were listed in the following table.

ABI Prism 7700 Sequence Detector (PE Biosystems). Thermal cycling was initiated with an initial setup for 50° C. for 2 minutes, followed by a first denaturation step at 95° C. for 10 minutes and then 40 cycles of 95° C. for 15 seconds (denaturation) and 60° C. for 1 minute (annealing and extension). GAPDH was used as an internal control for cDNA input. For GAPDH, amplification was performed with an initiation step of 2 minutes at 50° C., a first denaturation step of heating at 95° C. for 10 minutes, and then 40 cycles of 95° C. for 20 seconds (denaturation) and 62° C. for 1 minute (annealing and extension). Real-time PCR amplification data were collected continuously and analyzed with the ABI Prism 7700 Sequence Detector. Relative gene expression to the control calibrator, and normalized to the internal control, was calculated by the $\Delta\Delta C_T$ method (ABI user bulletin number 2, PE Biosystem) (Cheung, et al., *Cancer Lett.*, 246:122-8 (2007)). All experiments were performed in triplicates.

TABLE 1

Primers and conditions for RT-PCR

| Gene | Primer | Sequence | Tem. | Cyc. | Size |
|---|---|---|---|---|---|
| IL-6 | IL-6-F | 5'-ATG AAC TCC TTC TCC ACA AGC GC-3' (SEQ. ID NO: 1) | 58° C. | 35 | 628 bp |
|  | IL-6-R | 5'-GAA GAG CCC TCA GGC TGG ACT G-3' (SEQ. ID NO: 2) |  |  |  |
| GAPDH | GAPDH-F | 5'-AAC GGA TTT GGC CGT ATT GG-3' (SEQ. ID NO: 3) | 58° C. | 35 | 657 bp |
|  | GAPDH-R | 5'-CTT CCC GTT CAG CTC TGG G-3' (SEQ. ID NO: 4) |  |  |  |
| gp130 | gp130-F | 5'-GAG GTG TGA GTG GGA TGG TGG-3' (SEQ. ID NO: 5) | 58° C. | 30 | 810 bp |
|  | gp130-R | 5'-GCT GCA TCT GAT TTG CCA AC-3' (SEQ. ID NO: 6) |  |  |  |
| IL-6Rα | IL-6Rα-F | 5'-CAG CTG AGA ACG AGG TGT CC-3' (SEQ. ID NO: 7) | 58° C. | 35 | 219 bp |
|  | IL-6Rα-R | 5'-GCA GCT TCC ACG TCT TCT TGA-3' (SEQ. ID NO: 8) |  |  |  |
| Q-PCR |  |  |  |  |  |
|  | GAPDH-F | 5'-GAA GGT GAA GGT CGG AGT C-3' (SEQ. ID NO: 9) |  |  |  |
|  | GAPDH-R | 5'-GAA GAT GGT GAT GGG ATT TC-3' (SEQ. ID NO: 10) |  |  |  |
|  | Reporter dye: FAM | 5'-CAA GCT TCC CGT TCT CAG CC-3' (SEQ. ID NO: 11) |  |  |  |

Immunoblot Analysis

Immunoblot analysis was performed with gp130 ubiquitinylation. MH7A cells are incubated with 100 µM As$_2$O$_3$ for 0, 4 or 6 hours. Antibody to gp130 is used for immunoprecipitation (IP) of total cell lysates, followed by Western blot analysis with anti-ubiquitin antibodies FK1 and FK2. IP with non-immune rabbit serum (NIS) serves as control.

Quantitative RT-PCR

Figure 2A:
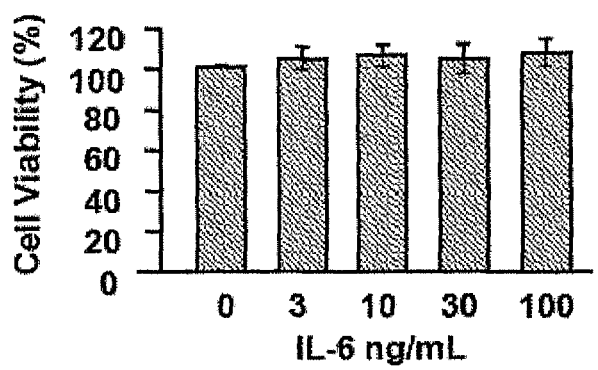
FIG. 2A is a bar graph showing viability of MH7A cells in the presence of increasing concentrations of IL-6 for 72 hours, as assessed by MTT assays. Data are expressed as cell viability (%) as a function of IL-6 concentration (ng/ml). Error bars represent the standard error of the mean (SEM) (n=3).
Figure 2B:
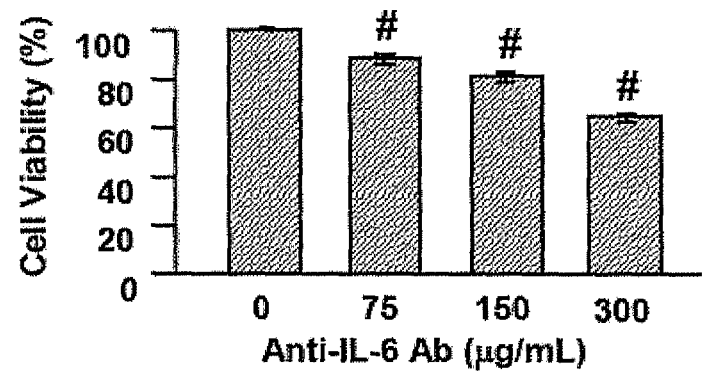
FIG. 2B is a bar graph showing viability of MH7A cells in the presence of increasing concentrations of anti-IL-6 Ab for 6 days, as assessed by MTT assays. Data are expressed as cell viability (%) as a function of anti-IL-6 Ab concentration (μg/ml). Error bars represent the standard error of the mean (SEM) (n=3) (**=P<0.001).
Figure 2C:
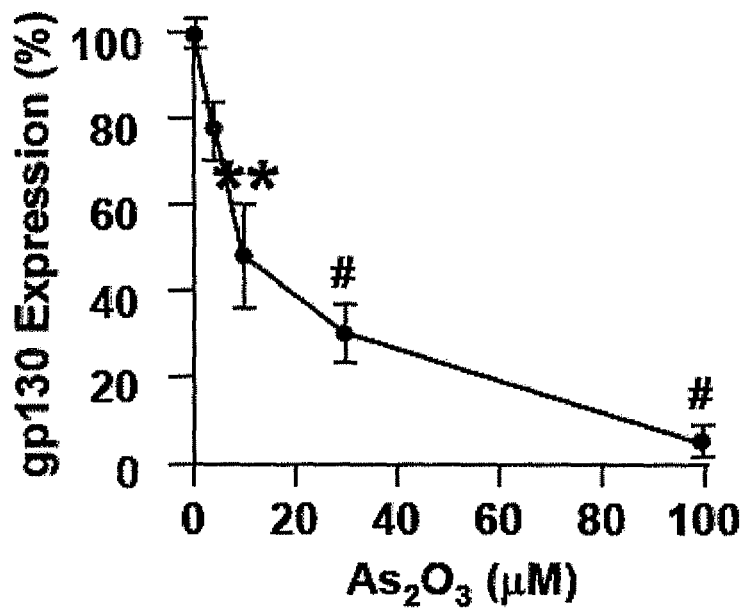
FIG. 2C is a line graph showing the effects of increasing concentrations of $As_2O_3$ on expression of gp130 when treated for 24 hours, as assessed by Western blot. Data are expressed as gp130 expression (%) as a function of $As_2O_3$ concentration (μM). Error bars represent the standard error of the mean (SEM) (n=3) (#=P<0.001; **=P<0.01).
Figure 2D:
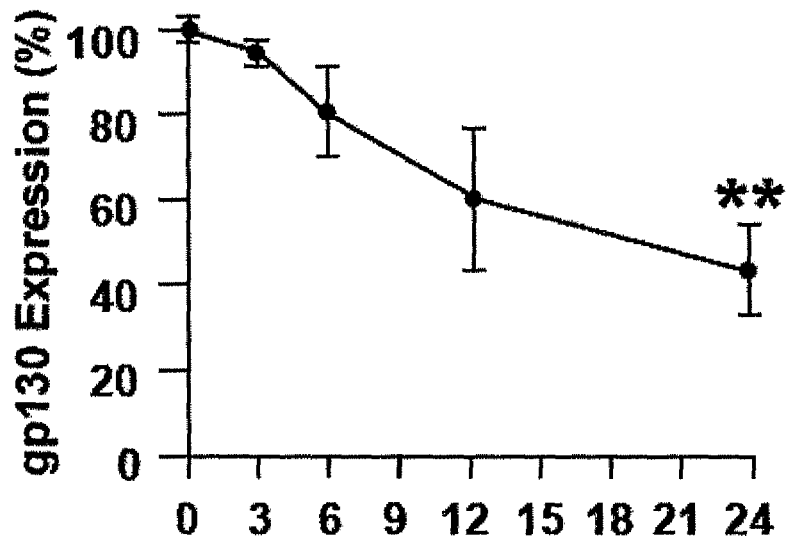
FIG. 2D is a line graph showing the effects of 5 μM $As_2O_3$ on expression of gp130 when treated for 0, 3, 6, 12 or 24 hours, as assessed by Western blot. Data are expressed as gp130 expression (%) as a function of time (hours). Error bars represent the standard error of the mean (SEM) (n=3) (**=P<0.01).

Quantitative-RT-PCR (Q-PCR) for GP130 was performed with the Assays-on-Demand™ Gene Expression System (AssayID: Hs00174360_m1, PE Biosystems, Foster City, Calif., USA) according to the manufacturer's instructions. The reaction mix contained 2 µL of cDNA, 10 µL of TaqMan® Universal PCR Master Mix, 1 µL of Assay-on-Demand™ Gene Expression Assay Mix, and RNase-free water to a volume of 20 µL. Q-PCR was performed with the Results:

To investigate if MH7A proliferation might be IL-6 dependent, the effects of IL-6 on cellular proliferation were investigated. Exogenous IL-6 did not increase the proliferation of MH7A cells (FIG. 2A). The effect of an IL-6 neutralizing antibody on cellular proliferation was then investigated. Interestingly, the results indicated that IL-6 neutralization led to significant inhibition of MH7A proliferation (FIG. 2B). As$_2$O$_3$-induced gp130 ubiquitination is shown by FK2 that recognizes both mono- and poly-ubiquitinated proteins, but not FK1 that recognizes poly-ubiquitinated proteins. These results demonstrates that gp130 is mono-ubiquitinated.

Semi-quantitative reverse transcription polymerase chain reaction (RT-PCR) confirmed that the IL-6 gene was actively transcribed in MH7A cells. These results suggest that an autocrine IL-6 loop might be involved in the proliferation of MH7A.

Figure 2E:
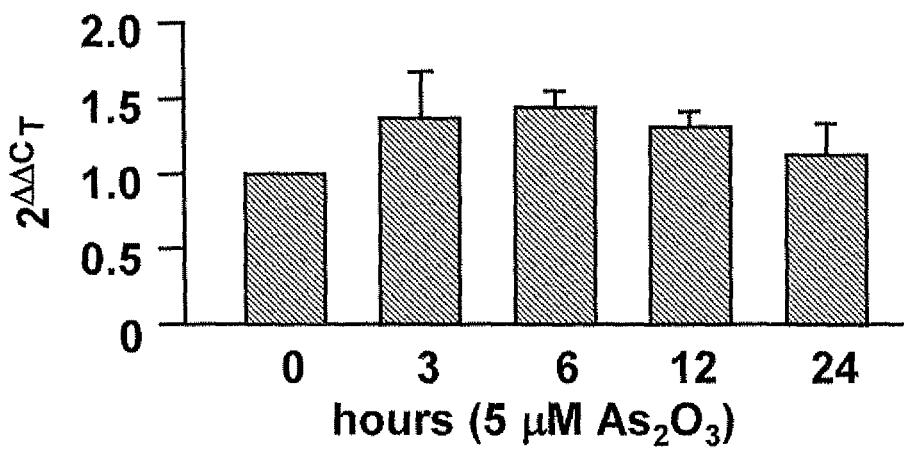
FIG. 2E is a bar graph showing the effects of 5 μM $As_2O_3$ on expression of gp130 when treated for 0, 3, 6, 12 or 24 hours, as assessed by quantitative-polymerase chain reaction (Q-PCR). Error bars represent the standard error of the mean (SEM) (n=3).

Example 3. $As_2O_3$ Post-Transcriptionally Down-Regulates gp130 of the IL-6 Receptor Complex Materials and Methods:
Materials and methods were as described in Examples 1-3, above.
Results:
To investigate if the inhibitory actions of $As_2O_3$ might be mediated via targeting of the IL-6 autocrine pathway, the effect of $As_2O_3$ on IL-6 transcription was first investigated. The results showed that $As_2O_3$ did not affect IL-6 gene transcription. The effects of $As_2O_3$ on the IL-6 receptor, comprising the two subunits IL-6 receptor α and gp130, were then examined. Western blot analysis showed that both subunits were expressed. Treatment with $As_2O_3$ resulted in a dose and time dependent decrease of gp130, with IL-6α remaining unchanged. Semi-quantitative RT-PCR showed that IL-6 receptor α and gp130 were actively transcribed, and that treatment with $As_2O_3$ had no effect on the transcription of both genes. To further verify these results, real-time quantitative polymerase chain reaction for the GP130 gene was performed. The results confirmed that $As_2O_3$ treatment had no effect on GP130 gene transcription (FIG. 2E). These findings implied that $As_2O_3$ targeted the IL-6 signaling pathway in MH7A, by down-regulation of the gp130 component of the IL-6 receptor complex at the post-transcriptional level.

Example 4. $As_2O_3$ Induces Degradation of gp130 Through the Lysosomal Pathway

Figure 3A:
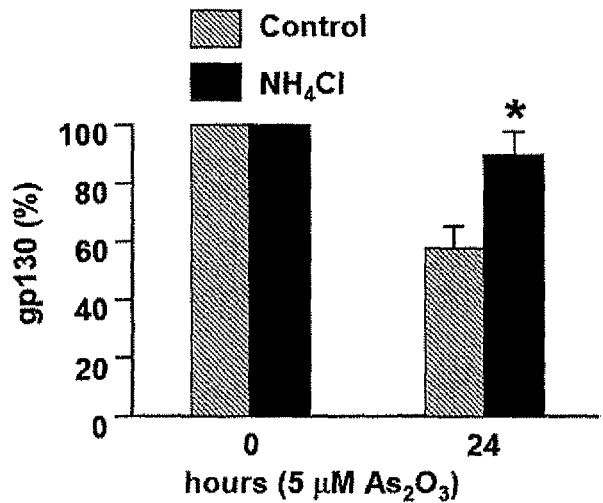
FIG. 3A is a bar graph showing the effect of the lysosome inhibitor $NH_4Cl$ (2.5 mM) on suppression of gp130 expression by 5 μM $As_2O_3$. Error bars represent the standard error of the mean (SEM) (n=3) (*=P<0.05).

Materials and Methods:
Materials and methods were as described in Examples 1-3, above.
Results:
The $As_2O_3$-mediated post-transcriptional down-regulation of gp130 suggested that degradation of gp130 might be enhanced. To address this issue, three pathways of protein degradation, lysosomal, proteasomal, and caspase-dependent proteolysis, were examined. Pre-incubation of MH7A cells with 2.5 mM $NH_4Cl$, a lysosome inhibitor, significantly prevented $As_2O_3$-induced decrease in gp130 (FIG. 3A). On the other hand, pre-incubation with the proteasome inhibitor MG115 (10 μM) and the caspase inhibitor Z-VAD-FMK (25 μM) had no effect on $As_2O_3$-induced decrease of gp130. These findings suggested lysosomal degradation to be involved in $As_2O_3$-induced decrease of gp130.

Example 5. $As_2O_3$ Induces Ubiquitination of gp130

Figure 3B:
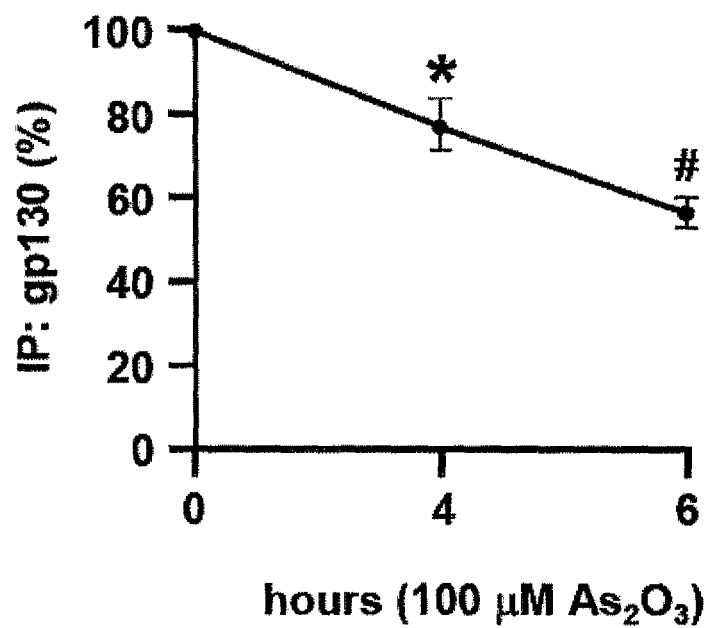
FIG. 3B is a line graph showing levels of gp130 immunoprecipitated (IP) from MH7A cells following treatment with 100 μM $As_2O_3$ for 0, 4 or 6 hours, Antibody to gp130 was used for immunoprecipitation (IP) of total cell lysates, followed by Western blot analysis with anti-ubiquitin antibodies FK1 and FK2. IP with non-immune rabbit serum (NIS) served as control. $As_2O_3$-induced gp130 ubiquitination was shown by FK2 that recognized both mono- and poly-ubiquitinated proteins, but not FK1 that recognized poly-ubiquitinated proteins. Error bars represent the standard error of the mean (SEM) (n=3) (*=P<0.05; #=P<0.001).

Materials and Methods:
Immunoprecipitation
Immunoprecipitation was performed by standard procedures (Pang et al., *Gastroenterology*, 132:1088-103 (2007)). Cells were washed with ice-cold PBS supplemented with 1 mM sodium orthovanadate and Complete protease inhibitor cocktail (Complete; Roche Molecular Biochemicals), and lysed with buffer (50 mM Tris-HCl, pH: 7.5, 100 mM NaCl, 1% Triton X-100, 4 μg/mL aprotinin, 100 μM phenylmethylsulfonyl fluoride, 200 μM sodium orthovanadate, 2 μg/mL leupeptin, 1 mM ditheiothreitol, and 1× Complete) at 4° C. for 15 minutes. Lysates were collected and centrifuged. Proteins were assayed (Bio-Rad Protein Assay Kit, Philadelphia, Pa., USA), and adjusted to 1 μg/μL (typically 800 to 1000 μg). Immunoprecipitation was preformed by incubating protein samples with the appropriate antibodies (typically 4 μg) or control non-immune sera at 4° C. overnight with gentle shaking. The antibody-protein complex was precipitated by incubation with 30 μL of rec-Protein G SEPHAROSE Beads® (Invitrogen) at 4° C. for 2 hours with gentle shaking. Protein G beads were then washed 3 times with 500 μL of ice-cold lysis buffer. The supernatant was aspirated, and 50 μL of 2× Laemmli buffer added. The antibody-protein complex was released from the beads by heating at 95° C. for 10 minutes. The immunoprecipitates were then analyzed by Western blotting in triplicates Results:
The addition of mono-ubiquitin moieties to a protein enables it to be sorted to lysosomes where it is finally degraded. To investigate if $As_2O_3$ increased gp130 ubiquitination, cell lysates from MH7A cells before and after $As_2O_3$ treatment were immunoprecipitated with an anti-gp 130 antibody, followed by Western blot analysis with the antibodies FK1 that recognized poly-ubiquitinated proteins, and FK2 that recognized both mono-ubiquintinated and poly-ubiquitinated proteins. The results showed that ubiquitinated gp130 was only detected (as a high molecular weight smear) in immunoblots with FK2, and not with FK1. Therefore, $As_2O_3$ induced mono-ubiquitination of gp130. Moreover, an increased amount of ubiquitinated gp130 was obtained with longer $As_2O_3$ treatment, suggesting a time-dependent mono-ubiquitination (FIG. 3B). These findings further confirmed that $As_2O_3$ induced lysosomal degradation of gp130.

Figure 4A:
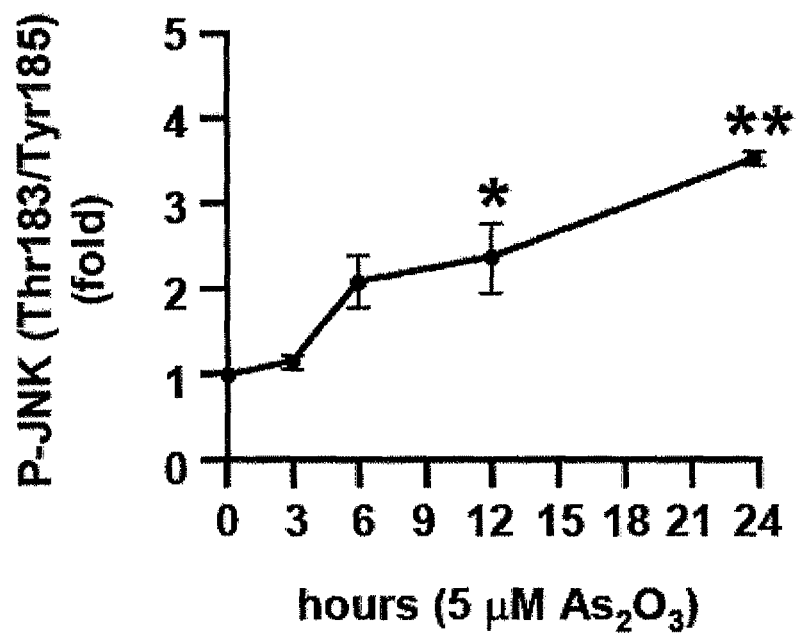
FIG. 4A is a line graph showing phosphorylation of JNK following treatment of MH7A cells with 5 μM $As_2O_3$ for 0, 3, 6, 12 or 24 hours as determined by Western blot. Values represent mean signal density±SEM (n=3) (*=P<0.05; **=P<0.01).
Figure 4B:
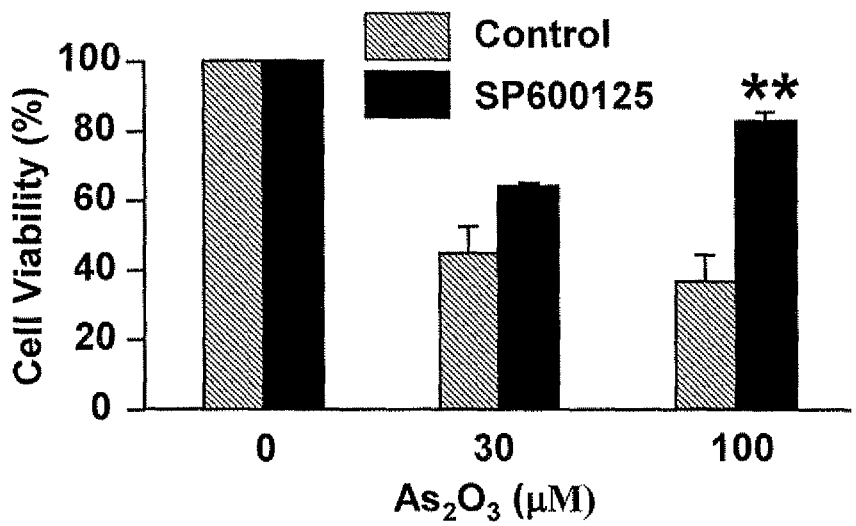
FIG. 4B is a bar graph showing viability of MH7A cells in the presence or absence of the JNK inhibitor SP600125 (30 μM) and in the presence of 0, 30 or 100 μM $As_2O_3$ over 24 hours, as assessed by MTT assays. Data are expressed as cell viability (%). Error bars represent the standard error of the mean (SEM) (n=3) (**=P<0.01).

Example 6. $As_2O_3$ Activation of the c-Jun-Terminal-N Kinase (JNK) is Involved in Suppression of IL-6 Signaling Materials and Methods:
Materials and methods were as described in Examples 1-5, above.
Results:
One of the important IL-6 signaling cascades is the MAPK pathway, including activation of JNK (Heinrich, et al., *Biochem. J*, 374:1-20 (2003)). Interestingly, in other cellular systems, arsenic has also been shown to activate JNK (Davison, et al., *Blood*, 103:3496-502 (2004)). The possible involvement of JNK activation in $As_2O_3$-induced suppression of IL-6 signaling in MH7A cells was therefore investigated. $As_2O_3$ treatment resulted in significant increases in JNK phosphorylation and hence its activation (FIG. 4A). Pre-treatment with the JNK inhibitor SP600125 (30 μM) prevented $As_2O_3$-induced increase in JNK phosphorylation. JNK activation was biologically relevant, as inhibition of $As_2O_3$-induced JNK activation significantly prevented $As_2O_3$-mediated suppression of MH7A cellular proliferation (FIG. 4B).

Figure 5A:
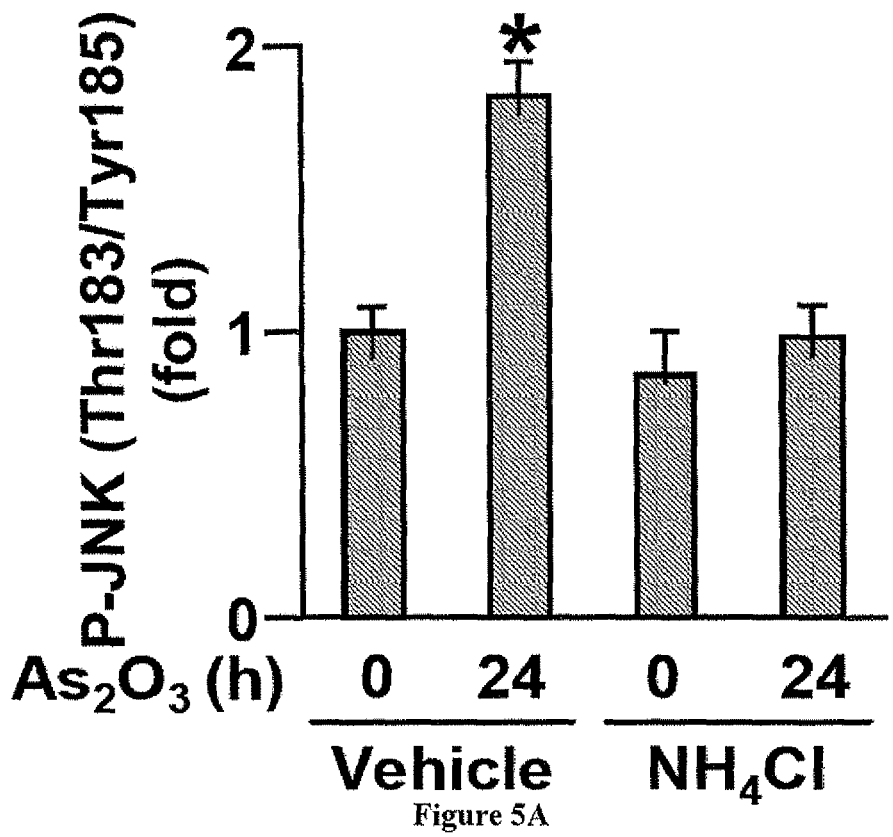
FIG. 5A is a bar graph showing the effect of the lysosome inhibitor $NH_4Cl$ (2.5 mM) on activation of JNK phosphorylation by 5 μM $As_2O_3$. Error bars represent the standard error of the mean (SEM) (n=3) (*=P<0.05).
Figure 5B:
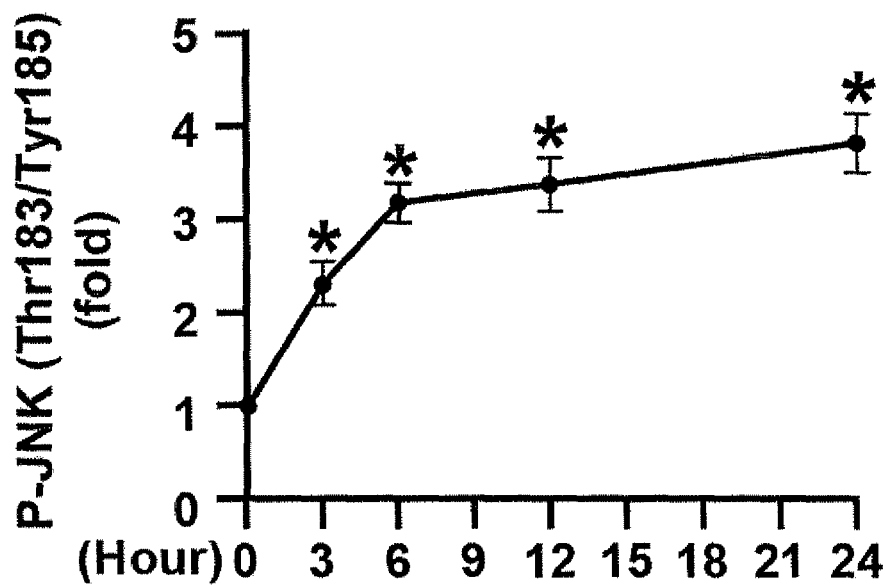
FIG. 5B is a line graph showing the effect of treatment of MH7A cells with 0.5 μg/ml anti-IL-6 Ab for 24 hours on phosphorylation of JNK as determined by Western blotting. Error bars represent one-way ANOVA with Dunnett's post-tests (n=3) (*=P<0.05).

To examine if JNK activation was related to suppression of IL-6 signaling, MH7A cells were treated with the lysosomal inhibitor $NH_4Cl$ (2.5 mM), which had previously been shown to rescue gp130 from $As_2O_3$-induced suppression. In the presence of $NH_4Cl$, $As_2O_3$-induced JNK activation was almost totally abrogated (FIG. 5A), suggesting that suppression of the IL-6 signaling pathway via degradation of gp130 was necessary for JNK activation. This point was directly demonstrated by treatment of MH7A cells with an IL-6 neutralizing antibody (0.5 μg/mL). As shown in FIG. 5B, IL-6 neutralization induced JNK activation. These results indicated that disruption of IL-6 signaling was needed for JNK activation in MH7A cells.

Example 7. $As_2O_3$-Induced JNK Activation Might Induce Growth Arrest Via the p53 Pathway Materials and Methods:
Cell Cycle Analysis Cell cycle analysis was performed as described (Pang et al., *J. Pathol.* 210:19-25, (2006)), Cells were trypsinized, washed twice with ice-cold PBS, re-suspended in 500 μL PBS, and stained with PI for 10 minutes on ice (DNA Prep™, Beckman Coulter). Cell cycle was determined by flow cytometry, and data analyzed by the WinMDI 2.8 software.

Figure 5C:
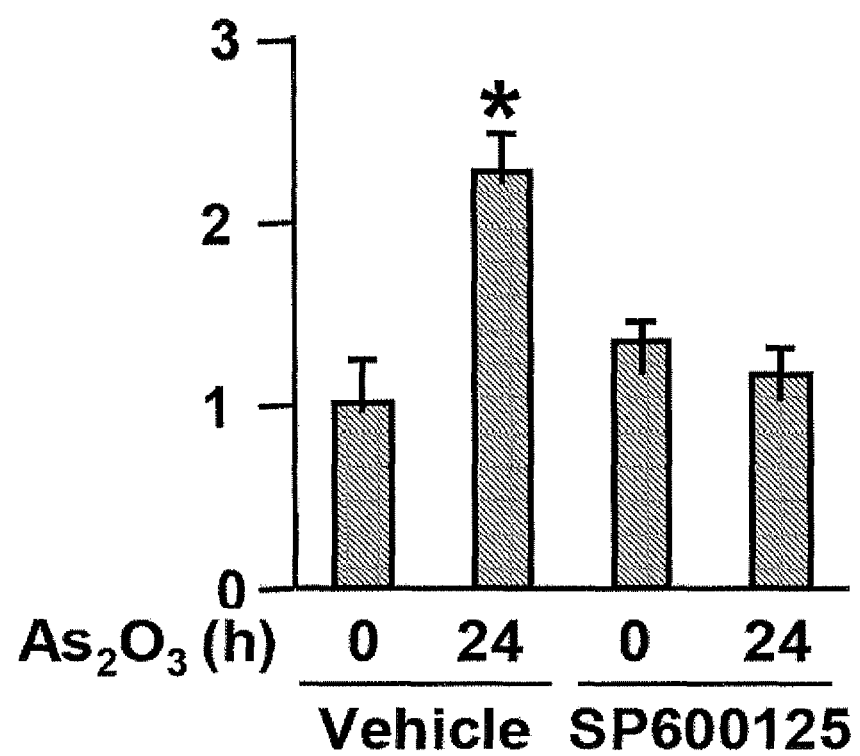
FIG. 5C is a bar graph showing the effect of the JNK inhibitor SP600125 (30 μM) on phosphorylation of p53 on serine-46 by 5 μM $As_2O_3$, as determined by Western blotting. Error bars represent one-way ANOVA with Dunnett's post-tests (n=3) (*=P<0.05).

Results:

To investigate if the growth inhibitory effect of $As_2O_3$-induced JNK activation might be mediated through caspase-3, MH7A cells were treated with the JNK inhibitor SP600125 (30 μM) before $As_2O_3$ treatment. INK inhibition did not affect $As_2O_3$-induced caspase-3 activation, suggesting that a caspase-independent pathway leading to growth inhibition might be involved in $As_2O_3$-induced INK activation. This observation was consistent with the results shown in FIGS. 1A-1C. As JNK is known to phosphorylate p53, and phosphorylation of p53 is a critical step in inducing growth arrest (Wu, *Cancer Biol. Ther.*, 3:156-61 (2004)), the effects of $As_2O_3$ on p53 phosphorylation were examined. As shown in FIG. 5C, $As_2O_3$ treatment significantly increased p53 phosphorylation at serine 46, an important site for transactivation of pro-apoptotic genes (Wu, *Cancer Biol. Ther.*, 3:156-61 (2004)). Inhibition of JNK activation with SP600125 significantly suppressed $As_2O_3$-mediated p53 phosphorylation, confirming p53 phosphorylation to be a down-stream effector of $As_2O_3$-induced JNK activation. Analysis of cell cycle showed that $As_2O_3$ treatment led to a significant G2M arrest. Histograms were used to show the effect of treatment of MH7A cells with 5 μM $As_2O_3$ over 24 hours, as determined by cell labeling with PI and flow cytometry.

Example 8. $As_2O_3$ Suppresses the JNK Cross-Talk Partner Nuclear Factor-kappaB (NFκB)

Materials and Methods:
Materials and methods were as described in Examples 1-7, above.

Figure 6A:
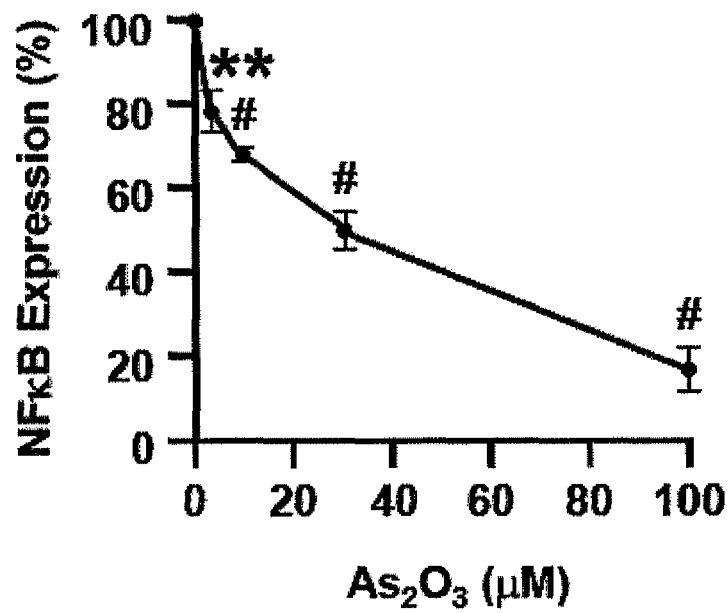
FIG. 6A is a line graph showing the effects of increasing concentrations of $As_2O_3$ on expression of NFκB when treated for 24 hours, as assessed by Western blot. Data are expressed as NFκB expression (%) as a function of $As_2O_3$ concentration (μM). Error bars represent the standard error of the mean (SEM) (n=3) (#=P<0.001; **=P<0.01).
Figure 6B:
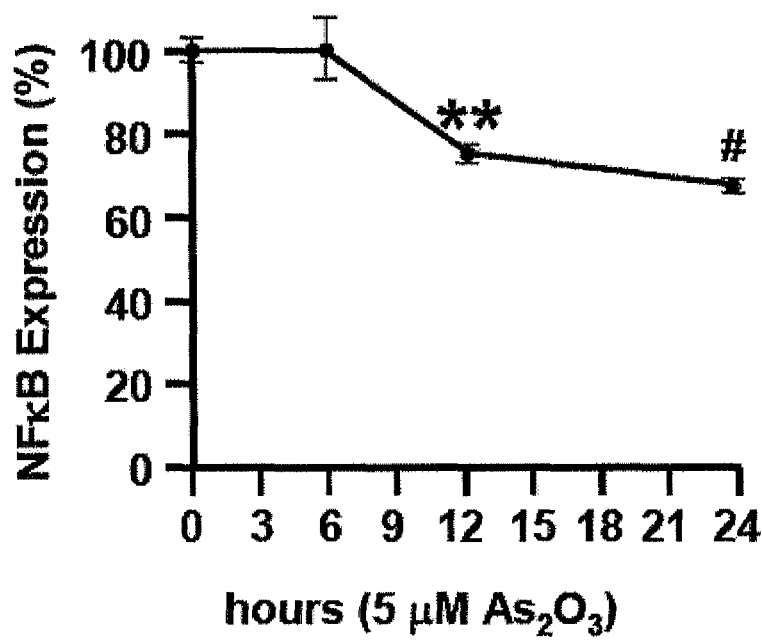
FIG. 6B is a line graph showing the effects of 5 μM $As_2O_3$ on expression of NFκB when treated for 0, 6, 12 or 24 hours, as assessed by Western blot, Data are expressed as NFκB expression (%) as a function of time (hours). Error bars represent the standard error of the mean (SEM) (n=3) (#=P<0.001; **=P<0.01).

Results:

Another important cross-talk partner of JNK is NFκB (Liu and Lin, *Oncogene*, 26:3267-78 (2007)). NFκB is also an important pro-inflammatory factor in arthritis (Simmonds, et al., *Rheumatology*, 47:584-90 (2008)). As shown in FIGS. 6A and 6B, NFκB was constitutively expressed in MI-17A. $As_2O_3$ treatment significantly decreased the level of NFκB in a dose (FIG. 6A) and time (FIG. 6B) dependent manner.

Modifications and variations will be apparent to those skilled in the art and are intended to come within the scope of the appended claims.

---

I claim:

1. A method for degradation of IL-6 receptor expressed in fibroblast-like synoviocytes in a human subject with arthritis, the method comprising
administering to the human subject with arthritis an oral dosage unit containing between about 1 and 10 mg arsenic trioxide, wherein the administered oral dosage unit of arsenic causes degradation of IL-6 receptor by degrading the gp130 subunit without causing degradation of the IL-6 receptor α subunit of the IL-6 receptor expressed in fibroblast-like synoviocytes in the human subject with arthritis.

2. The method of claim 1, wherein the fibroblast-like synoviocytes are in a patient with rheumatoid arthritis.

3. The method of claim 1, wherein the fibroblast-like synoviocytes are in a patient with non-rheumatoid inflammatory arthritis.

4. The method of claim 1, further comprising administering a steroidal or non-steroidal anti-inflammatory agent.

5. The method of claim 1, wherein the dosage unit contains between 5 and 10 mg arsenic trioxide.

6. The method of claim 1, wherein the administered oral dosage unit of arsenic causes reduction of proliferation of fibroblast-like synoviocytes in the human subject with arthritis by a caspase-independent pathway.

7. The method of claim 1, wherein the administered oral dosage unit of arsenic causes degradation of IL-6 receptor by degrading the gp130 subunit without causing degradation of the IL-6 receptor a subunit of the IL-6 receptor expressed in fibroblast-like synoviocytes in the human subject with arthritis and reduction of proliferation of fibroblast-like synoviocytes in the human subject with arthritis.

8. A method comprising administering to a human subject with arthritis an oral dosage unit containing between about 1 and 10 mg arsenic trioxide wherein the administered oral dosage unit of arsenic causes degradation of IL-6 receptor by degrading the gp130 subunit without causing degradation of the IL-6 receptor a subunit of the IL-6 receptor expressed in fibroblast-like synoviocytes.

9. The method of claim 1, wherein the degradation of IL-6 receptor comprises degrading component gp130 of the IL-6 receptor by at least 20% when compared to the level of gp130 of the IL-6 receptor expressed in fibroblast-like synoviocytes of the human subject with arthritis before administration of the oral dosage unit of arsenic trioxide.

10. The method of claim 1, wherein the degradation is via mono-ubiquitination of the gp130 subunit of the IL-6 receptor expressed in the fibroblast-like synoviocytes in the human subject with arthritis.

11. The method of claim 1, wherein the administered oral dosage unit of arsenic causes mono-ubiquitination of the gp130 subunit of the IL-6 receptor and its degradation via the lysosomal pathway in the fibroblast-like synoviocytes in the human subject with arthritis.

12. The method of claim 1, wherein the administered oral dosage unit of arsenic causes degradation of the gp130 subunit in the absence of degradation of the IL-6 receptor a subunit of the IL-6 receptor expressed in the fibroblast-like synoviocytes in the human subject with arthritis.

13. A method for degradation of IL-6 receptor expressed in fibroblast-like synoviocytes in a human subject with arthritis, the method comprising
administering to the human subject with arthritis an oral dosage unit containing an amount of arsenic trioxide sufficient to cause, when administered to the human subject with arthritis, degradation of IL-6 receptor by degrading the gp130 subunit without causing degradation of the IL-6 receptor a subunit of the IL-6 receptor expressed in fibroblast-like synoviocytes in the human subject with arthritis,
wherein the administered oral dosage unit of arsenic causes degradation of IL-6 receptor expressed in fibroblast-like synoviocytes in the human subject with arthritis.

14. The method of claim 13, wherein the oral dosage unit of arsenic contains an amount of arsenic trioxide sufficient to cause, when administered to the human subject with arthritis, reduction of proliferation of fibroblast-like synoviocytes in the human subject with arthritis, wherein the administered oral dosage unit of arsenic causes reduction of proliferation of fibroblast-like synoviocytes in the human subject with arthritis.

15. The method of claim 13, wherein the oral dosage unit of arsenic contains an amount of arsenic trioxide sufficient to cause, when administered to the human subject with arthritis, degradation of IL-6 receptor by degrading the gp130 subunit without causing degradation of the IL-6 receptor a subunit of the IL-6 receptor expressed in fibroblast-like synoviocytes in the human subject with arthritis and reduction of proliferation of fibroblast-like synoviocytes in the human subject with arthritis, wherein the administered oral dosage unit of arsenic causes degradation of IL-6 receptor by degrading the gp130 subunit without causing degradation of the IL-6 receptor a subunit of the IL-6 receptor expressed in fibroblast-like synoviocytes in the human subject with arthritis and reduction of proliferation of fibroblast-like synoviocytes in the human subject with arthritis.

16. The method of claim 13, wherein the amount of arsenic trioxide is adjusted lower according to kidney function of the human subject with arthritis.

17. The method of claim 8, wherein the administered oral dosage unit of arsenic trioxide reduces proliferation of fibroblast-like synoviocytes in the human subject with arthritis.

18. A method for degradation of IL-6 receptor expressed in fibroblast-like synoviocytes in a human subject with arthritis, the method comprising
   administering to the human subject with arthritis an oral dosage unit of arsenic trioxide containing an amount of arsenic trioxide effective to cause degradation of the gp130 subunit in the absence of degradation of the IL-6 receptor a subunit of the IL-6 receptor expressed in fibroblast-like synoviocytes in the human subject with arthritis.

19. The method of claim 18, wherein the amount of arsenic trioxide effective to cause degradation of the gp130 subunit in the absence of degradation of the IL-6 receptor α subunit of the IL-6 receptor is between about 1 mg and 10 mg arsenic trioxide.

20. A method of inhibiting fibroblast-like synoviocyte cell proliferation in a human subject with arthritis, the method comprising
   administering to the human subject with arthritis an oral dosage unit of arsenic trioxide containing an amount of arsenic trioxide effective to inhibit fibroblast-like synoviocyte cell proliferation via a caspase-independent pathway.

21. The method of claim 20, wherein the amount of arsenic trioxide is effective to inhibit fibroblast-like synoviocyte cell proliferation via a caspase-independent and IL-6 receptor-dependent pathway.

22. The method of claim 20, wherein the amount of arsenic trioxide effective to inhibit fibroblast-like synoviocyte cell proliferation in a caspase-independent pathway is between about 1 mg and 10 mg arsenic trioxide.

* * * * *

SEQUENCE LISTING

<160> NUMBER OF SEQ ID NOS: 11

<210> SEQ ID NO 1
<211> LENGTH: 23
<212> TYPE: DNA
<213> ORGANISM: Artificial Sequence
<220> FEATURE:
<223> OTHER INFORMATION: Synthetic primer

<400> SEQUENCE: 1
atgaactcct tctccacaag cgc          23

<210> SEQ ID NO 2
<211> LENGTH: 22
<212> TYPE: DNA
<213> ORGANISM: Artificial Sequence
<220> FEATURE:
<223> OTHER INFORMATION: Synthetic primer

<400> SEQUENCE: 2
gaagagccct caggctggac tg           22

<210> SEQ ID NO 3
<211> LENGTH: 20
<212> TYPE: DNA
<213> ORGANISM: Artificial Sequence
<220> FEATURE:
<223> OTHER INFORMATION: Synthetic primer

<400> SEQUENCE: 3
aacggatttg gccgtattgg              20

<210> SEQ ID NO 4
<211> LENGTH: 19

<212> TYPE: DNA
<213> ORGANISM: Artificial Sequence
<220> FEATURE:
<223> OTHER INFORMATION: Synthetic primer

<400> SEQUENCE: 4
cttcccgttc agctctggg                                            19

<210> SEQ ID NO 5
<211> LENGTH: 21
<212> TYPE: DNA
<213> ORGANISM: Artificial Sequence
<220> FEATURE:
<223> OTHER INFORMATION: Synthetic primer

<400> SEQUENCE: 5
gaggtgtgag tgggatggtg g                                         21

<210> SEQ ID NO 6
<211> LENGTH: 20
<212> TYPE: DNA
<213> ORGANISM: Artificial Sequence
<220> FEATURE:
<223> OTHER INFORMATION: Synthetic primer

<400> SEQUENCE: 6
gctgcatctg atttgccaac                                           20

<210> SEQ ID NO 7
<211> LENGTH: 20
<212> TYPE: DNA
<213> ORGANISM: Artificial Sequence
<220> FEATURE:
<223> OTHER INFORMATION: Synthetic primer

<400> SEQUENCE: 7
cagctgagaa cgaggtgtcc                                           20

<210> SEQ ID NO 8
<211> LENGTH: 21
<212> TYPE: DNA
<213> ORGANISM: Artificial Sequence
<220> FEATURE:
<223> OTHER INFORMATION: Synthetic primer

<400> SEQUENCE: 8
gcagcttcca cgtcttcttg a                                         21

<210> SEQ ID NO 9
<211> LENGTH: 19
<212> TYPE: DNA
<213> ORGANISM: Artificial Sequence
<220> FEATURE:
<223> OTHER INFORMATION: Synthetic primer

<400> SEQUENCE: 9
gaaggtgaag gtcggagtc                                            19

<210> SEQ ID NO 10
<211> LENGTH: 20
<212> TYPE: DNA
<213> ORGANISM: Artificial Sequence
<220> FEATURE:
<223> OTHER INFORMATION: Synthetic primer

<400> SEQUENCE: 10

```
gaagatggtg atgggatttc                                                20

<210> SEQ ID NO 11
<211> LENGTH: 20
<212> TYPE: DNA
<213> ORGANISM: Artificial Sequence
<220> FEATURE:
<223> OTHER INFORMATION: Synthetic primer

<400> SEQUENCE: 11
caagcttccc gttctcagcc                                                20
```